US012773438B2

(12) United States Patent
Singh et al.

(10) Patent No.: US 12,773,438 B2
(45) Date of Patent: Oct. 27, 2026

(54) **METHOD OF EXTRACTION OF PROANTHOCYANIDINS COMPOUND FROM PINE BARK OF *PINUS ROXBURGHII***

(71) Applicant: AMBE PHYTOEXTRACTS PVT. LTD., Uttrakhand (IN)

(72) Inventors: Harshpal Singh, Uttarakhand (IN); Kul Bhaskar Singh, Uttarakhand (IN); Shashi Chandrama Singh, Uttarakhand (IN); Muskan Choudhary, Uttarakhand (IN); Shipra Agrawal, Uttarakhand (IN)

(73) Assignee: AMBE PHYTOEXTRACTS PVT. LTD., Uttrakhand (IN)

( * ) Notice: Subject to any disclaimer, the term of this patent is extended or adjusted under 35 U.S.C. 154(b) by 296 days.

(21) Appl. No.: 18/515,367

(22) Filed: Nov. 21, 2023

(65) Prior Publication Data

US 2024/0165182 A1 May 23, 2024

(30) Foreign Application Priority Data

Nov. 21, 2022 (IN) ............................ 202211066766

(51) Int. Cl.
*A61K 36/15* (2006.01)
*A61K 31/192* (2006.01)
*A61K 31/353* (2006.01)

(52) U.S. Cl.
CPC ............ *A61K 36/15* (2013.01); *A61K 31/192* (2013.01); *A61K 31/353* (2013.01); *A61K 2236/15* (2013.01); *A61K 2236/333* (2013.01); *A61K 2236/39* (2013.01); *A61K 2236/51* (2013.01); *A61K 2236/53* (2013.01); *A61K 2236/55* (2013.01)

(58) Field of Classification Search
CPC .... A61K 36/15; A61K 31/192; A61K 31/353; A61K 2236/15; A61K 2236/333; A61K 2236/39; A61K 2236/51; A61K 2236/53; A61K 2236/55
See application file for complete search history.

(56) References Cited

U.S. PATENT DOCUMENTS

| | | | | |
|---|---|---|---|---|
| 6,372,266 B1 * | 4/2002 | Suzuki | .................... | A61P 15/00 424/464 |
| 2011/0046215 A1 * | 2/2011 | Ferrari | .................. | A61K 36/15 514/456 |

FOREIGN PATENT DOCUMENTS

| | | | | |
|---|---|---|---|---|
| CN | 102086187 A | | 6/2011 | |
| CN | 102086187 B | * | 5/2012 | |
| KR | 20070103213 A | * | 10/2007 | ........... A23L 33/105 |

OTHER PUBLICATIONS

Seewald, E. The quantification of oligomeric proanthocyanidins in the inner and outer barks of selected B.C. conifers. M.S. Thesis, University of British Columbia, 1998. (retrieved from <URL: https://open.library.ubc.ca/soa/cIRcle/collections/ubctheses/831/items/1.0089195>, 151 pages. (Year: 1998).*

(Continued)

*Primary Examiner* — Anand U Desai
*Assistant Examiner* — Robert Franklin Spaine
(74) *Attorney, Agent, or Firm* — Carter, DeLuca & Farrell, LLP; George Likourezos

(57) ABSTRACT

A method for synthesis of method of extraction of proanthocyanidins compound from pine bark—of *Pinus roxburghii* comprising the steps: weighing and pulverizing bark to obtain pulverized powder, adding powder with water in steam jacketed rotary extractor to obtain an extract A, adding the residue in the extractor to obtain extract B, processing the second residue to obtain a third residue and an extract C which is further processed to obtain a third residue and extract D, mixing A, B, C, D extract to obtain liquor, subjecting vacuum concentrate and insoluble concentrate and subjecting to spray drying and vacuum drying respectively, sieving the powder followed by sterilization to obtain the Pine Bark Extract and further subjecting to HPLC analysis for proanthocyanidins content and packing the extract into fiber drums with double polybags for storage.

3 Claims, 9 Drawing Sheets

(56) References Cited

OTHER PUBLICATIONS

Phil, M.S., et al., KR 20070103213 A, machine translation, 13 pages (Year: 2007).*

Hellström, J.K.; Mattila, P.H. J. Agric. Food Chem. 2008, 5 (17), 7617-7624. doi: 10.1021/jf801336s (Year: 2008).*

Sarma, N.D.; Wayne, A.; ElSohly, M.A.; Brown, P.N.; Elzinga, S.; Johnson, H.E.; Marles, R.J.; Melanson, J.E.; Russo, E.; Deyton, L ; Hudalla, C; Vrdoljak, G.A.; Wurzer, J.H.; Khan, I.A.; Kim, N.; Giancaspro G.I. J. Nat. Prod. 2020, 83 (4), 1334-1351; doi: 10.1021/acs.jnatprod.9b01200 (Year: 2020).*

Singh, S.C.; Singh, K.B.; Singh, H. Journal of the Indian Chemical Society 2022 (ePub Jan. 1, 2022), 99 (2), 100325, pp. 1-7; doi: 10.1016/j.jics.2021.100325 (Year: 2022).*

Maritime Pine Extract—Safety Data Sheet (SDS), 1539803, rev. 4; U.S. Pharmacopeia: Rockville, MD, Jul. 7, 2023. <URL:https://store.usp.org/product/1539803>, 6 pages. (Year: 2023).*

Zhang et al., CN 102086187 B, machine translation, 10 pages (Year: 2012).*

Rauf, A.; et al. Proanthocyanidins: A comprehensive review. Biomedicine & Pharmacotherapy 2019, 116, 108999. DOI: 10.1016/j.biopha.2019.108999 (Year: 2019).*

Singh, S. C. et al. A controlled clinical study of product PINOROX® (Pinus roxburghii bark extract) (PINOROX®) as dietary supplement for enhanced physical performance. Journal of the Indian Chemical Society 2022, 99, 100325. DOI: 10.1016/j.jics.2021.100325 (Year: 2022).*

Singh, S. C. et al., “A controlled clinical study of product PINOROX® (Pinus roxburghii bark extract) (PINOROX®) as dietary supplement for enhanced physical performance” Journal of the Indian Chemical Society Feb. 2022) pp. 1-7, vol. 99, No. 2.

* cited by examiner

METHOD OF EXTRACTION OF PROANTHOCYANIDINS COMPOUND FROM PINE BARK OF *PINUS ROXBURGHII*

FIELD OF THE INVENTION

The present invention relates to a standardized method of extraction of proanthocyanidins compound from pine bark of *Pinus roxburghii* through hydroalcoholic extraction method for application in nutraceuticals or health supplement as an antioxidant that aids in increasing the endurance level in a healthy or a sport person while performing physical or athletic activities as well as support in reducing oxidative stress.

BACKGROUND OF THE INVENTION

*Pinus roxburghii* also known as chir pine/long leaf Indian pine is a dominant species in Himalayan region of India. The tree bark is usually in reddish brown in color with a thick diameter and leaves with needle like appearance. The tree naturally contains huge amount of polyphenols. The tree has several applications for human kind starting with the timber itself which is used for constructing furniture, oleoresin used in paints, pine needle oil used in cosmetic product, pine tree heart wood and root used in Indian ayurveda having clinical application-Karnaroga (Disease of ear), Kantharoga (Disease of throat), Aksiroga (Disease of eye), Daha (Burning sensation), Varana (Ulcer), Svarabheda (Hoarseness of voice) and many more. Pine bark in ayurveda is used for healthy skin, skin complexion promoter, wound healing, tinnitus, anti-microbial, anti-inflammatory and many more health benefits.

Traditionally, the *Pinus roxburghii* tree is composed of natural polyphenols that exhibits antioxidant effect when consumed to prevent oxidative stress as well as protect cells from free radical cell damages. The availability of *Pinus roxburghii* in India is in abundance and pine bark from it can be used as a substitute for proanthocyanidins source against the other *Pinus* species available globally with a brand name.

CN102086187B discloses a method for extracting and separating out oligomeric proanthocyanidins from Yunnan pine barks. The method is as follows: pre-treating raw materials, sorting out unpolluted parts in fresh Yunnan pine barks, drying indoors, controlling the moisture of the raw materials to be 8-10%, smashing, and sieving with a 20-mesh screen; extracting the pre-treated raw materials, adding a solvent in a solid-liquid ratio of 1:(2-10), and carrying out reflux extraction or microwave extraction for 1-4 times under the boiling condition; mixing extracted solution, drawing and filtering, concentrating filtrate into extract; finally separating, dissolving the extract by water the weight of which is 3-6 times that of the extracted raw materials, filtering, extracting and degreasing the filtrate for 2 times with chloroform, wherein the volume ratio of chloroform to extract aqueous dissolving solution is 1:3; adding sodium chloride in a degreased water layer until saturation is reached, extracting for 3 times with ethyl acetate, wherein the volume ratio of ethyl acetate to saturated water is 1:1; and removing the solvent from extract liquor at the temperature of 70±2° C. under the pressure of 0.02-0.08 MPa, and concentrating so as to obtain the oligomeric proanthocyanidins. In the method provided by the invention, the technological process is simple and practicable, the equipment is simple, the raw materials are available, and the method is convenient for popularization and application.

KR20070103213A discloses an isolation process of proanthocyanidin from the bark of pine tree is provided to improve purity of proanthocyanidin by performing hot water extraction followed by lower alcohol extraction, so that high purity proanthocyanidin is applicable to medicines, health supplement food and cosmetics. An isolation process of proanthocyanidin from the bark of pine tree comprises the steps of: extracting the bark of pine tree with hot water at 80-120° C. for 0.5-24 hours; filtering the extract of pine tree bark to remove precipitates; concentrating the filtered pine tree bark extract; and extracting the concentrate of pine tree bark extract with lower alcohol selected from methanol, ethanol, n-propanol, isopropanol, n-butanol, isobutanol, sec-butanol and n-pentanol.

Conventionally several methods for extracting proanthocyanidins from different Pine tree species are known. However, standardized extraction method of proanthocyanidins from pine bark of *Pinus roxburghii* has not yet been established. Due to the abundancy of Pine Tree—*Pinus roxburghii* in India, the pine bark may be used to extract proanthocyanidins compound and can be used as a functional ingredient in nutraceuticals or health/dietary supplement as a source of an antioxidant. There is no established standardized method of extraction of proanthocyanidins from pine bark of *Pinus roxburghii.*

In order to overcome the aforementioned drawbacks, there exists a need in the art to provide a standardized method for extraction of proanthocyanidins compound from Pine bark of *Pinus roxburghii*, which makes use of natural resources efficiently as well as having a clinical application such as antioxidant and anti-inflammatory properties, anti-ageing effect, boost brain health and cognition function, promote healthy skin, support in managing cardiovascular risks, boosts physical/athletic performances as well as increases endurance and many more health benefits.

OBJECTS OF THE INVENTION

The principal object of the present invention is to overcome the disadvantage of the prior art.

An object of the present invention is to develop a standardized method for extraction and estimation of proanthocyanidins compound from pine bark of *Pinus roxburghii.*

Another object of the present invention is to develop a standardized method that utilizes the pine bark from Pine tree—*Pinus roxburghii* for a healthcare segment which is available in abundance in the Indian forest.

Another object of the present invention is to develop a method of extraction of proanthocyanidins compound from pine bark extract obtained from *Pinus roxburghii* that utilizes natural resources in different formulation of nutraceuticals or health/dietary supplement that contributes in improving physical performances or activities, endurance, aerobic and anaerobic capacity as well as preventing any oxidative damages caused by free radical cells.

Another object of the present invention is to develop a method that prove that pine bark extract obtained from *Pinus roxburghii* possesses antioxidant properties.

Another object of the present invention is to develop a method that prove that pine bark extract obtained from *Pinus roxburghii* protect cells from oxidative damage done by free radicals.

Yet another object of the present invention is to recover solvent used in the method, which can be reused for extraction process again. This will make the process of extraction cost effective.

The foregoing and other objects, features, and advantages of the present invention will become readily apparent upon further review of the following detailed description of the preferred embodiment as illustrated in the accompanying drawings.

SUMMARY OF THE INVENTION

The present invention relates to a method of extraction of proanthocyanidins compound from pine bark extract obtained from *Pinus roxburghii*, through hydroalcoholic extraction method and estimation of proanthocyanidins compound having application in nutraceuticals or health supplement for enhancing the aerobic and anaerobic performance along with increased endurance and muscle power for performing different physical activities efficiently.

According to an embodiment of the present invention, a method for the extraction of the proanthocyanidins from pine bark of the Pine Tree—*Pinus roxburghii* comprises of following steps: a) the dried pine bark are weighed and pulverized, followed by sieving in order to obtain pulverized powder, b) to the powder 4 times of the 80% ethanol and RO (Reverse Osmosis) water are added in a jacketed rotary extractor at a temperature in the range of 70-80° C. for a time duration in the range of 100-140 minutes under circulation, followed by filtering through a filter in a clean, dry, and closed tank to obtain a first residue and an extract A, c) the first residue is processed with the 80% of ethanol is added in the steam jacketed rotary extractor at a temperature in the range of 70-80° C. for a time duration in the range of 100-140 minutes, followed by filtration in a separate clean, dry, and closed tank to obtain a second residue and an extract B, d) the obtained second residue is processed with the 80% ethanol in the steam jacketed rotary extractor for a time duration in the range of 100-140 minutes, followed by filtration in a separate clean, dry, and closed tank to obtain a third residue and an extract C, e) the obtained third residue is processed with the 80% ethanol in the steam jacketed rotary extractor for a time duration in the range of 100-140 minutes, followed by filtration in a separate clean, dry, and closed tank to obtain a third residue and an extract D.

According to an another embodiment of the present invention, the proposed method further comprises of following steps which includes: f) the obtained extract A, B, C, and D are mixed and hold at a temperature in the range of 5-15° C. for a time duration in the range of 20-28 hours in order to obtain a combined extract, followed by filtering the combined extract through centrifuge fitted with 3-5 micron nylon bag to remove insoluble fines and obtain a liquor, g) the obtained liquor is subjected to distillation under vacuum at a temperature in the range of 65-75° C. in a distillation kettle, followed by concentration of the liquor up to 25-30% TS (Total Solids) in order to obtain a concentrate, followed by holding the concentrate at a temperature of 10-15° C. for a time duration in the range of 20-28 hours for settling and filtering the concentrate through centrifuge to separate water insoluble solid mass and collect water soluble concentrate of phenolic compounds, h) the obtained water soluble concentrate are subjected to spray drying using a spray drier having inner chamber fixed at a temperature in the range of 185-190° C. and outer chamber fixed at a temperature in the range of 90-105° C., in order to obtain sterilized pine bark extract, i) the spray dried powder, grinding, and sieving are collected with the powder through #150 sieve, passing the extract through metal detector to avoid Ferrous, Non-Ferrous and stainless steel elements, followed by HPLC analysis for proanthocyanidins content and packing the extract into fiber drums with double polybags for storage.

After production of Pine bark extract (Pinorox®) from *Pinus roxburghii*, proanthocyanidins content in Pine bark Extract (obtained from *Pinus roxburghii*) was found to be ≥80% by HPLC.

While the invention has been described and shown with particular reference to the preferred embodiment, it will be apparent that variations might be possible that would fall within the scope of the present invention.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Figure 1:
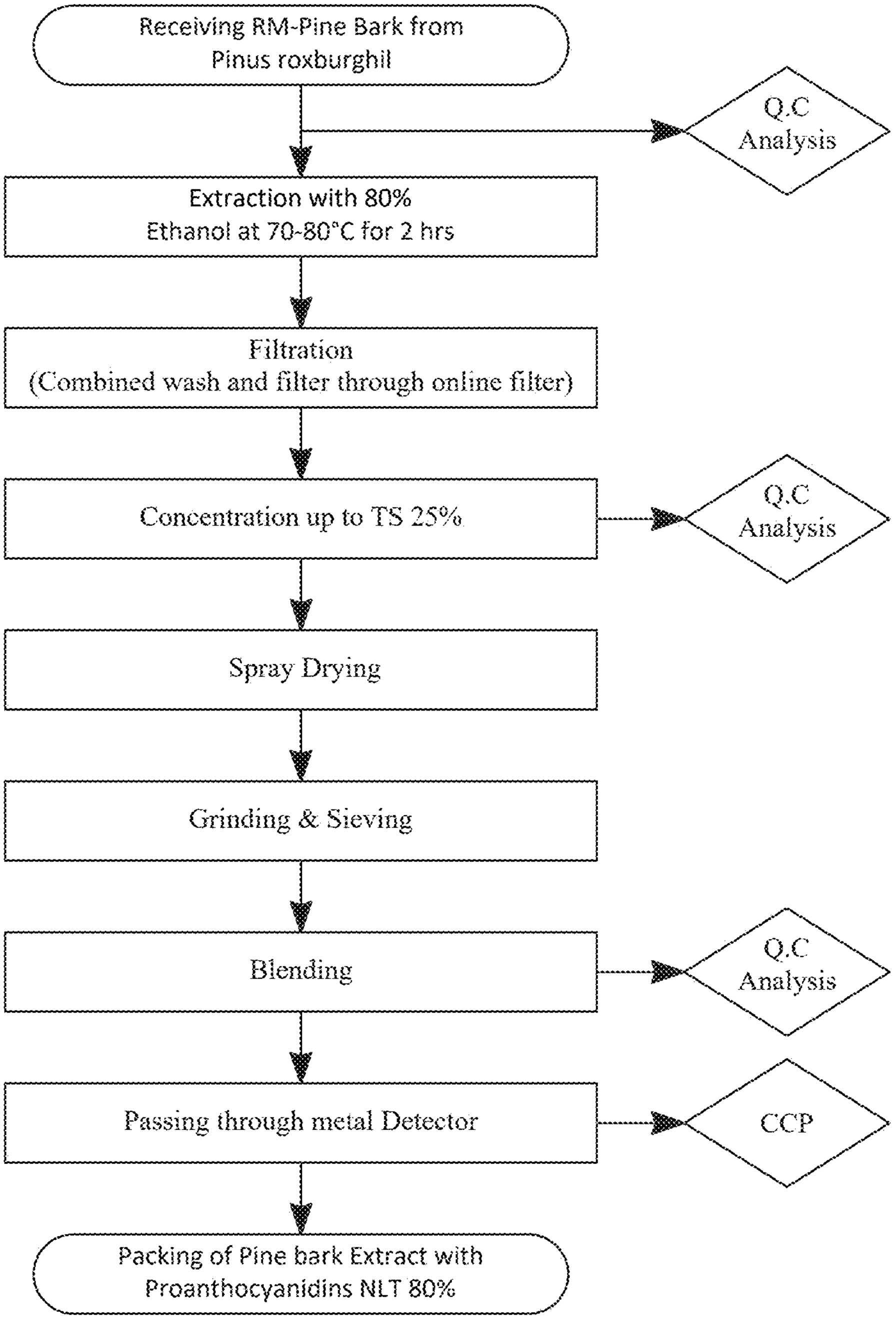
FIG. 1 illustrates a method for extraction of Pine bark obtained from *Pinus roxburghii;*

The following description includes the preferred best mode of one embodiment of the present invention. It will be clear from this description of the invention that the invention is not limited to these illustrated embodiments but that the invention also includes a variety of modifications and embodiments thereto. Therefore, the present description should be seen as illustrative and not limiting. While the invention is susceptible to various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

In any embodiment described herein, the open-ended terms "comprising," "comprises," and the like (which are synonymous with "including," "having" and "characterized by") may be replaced by the respective partially closed phrases "consisting essentially of," consists essentially of," and the like or the respective closed phrases "consisting of," "consists of, the like.

As used herein, the singular forms "a," "an," and "the" designate both the singular and the plural, unless expressly stated to designate the singular only.

The present invention relates to a method for extraction of the proanthocyanidins compounds from pine bark of the Pine Tree—*Pinus roxburghii* that utilizes a natural resource *Pinus roxburghii* pine bark for the formulation of a nutraceutical or health/dietary supplement that as an antioxidant.

According to an embodiment of the present invention, a method for the extraction of the proanthocyanidins from pine bark of the Pine Tree—*Pinus roxburghii* comprises of following steps: a) weight and pulverizing a dried pine bark, followed by sieving in order to obtain pulverized powder, b) adding the powder 4 times of the 80% ethanol and RO (Reverse Osmosis) water in a jacketed rotary extractor at a temperature in the range of 70-80° C. for a time duration in the range of 100-140 minutes under circulation, followed by filtering through a filter in a clean, dry, and closed tank in to obtain a first residue and an extract A, c) adding the first residue with the 80% of ethanol in the steam jacketed rotary extractor at a temperature in the range of 70-80° C. for a time duration in the range of 100-140 minutes, followed by filtration in a separate clean, dry, and closed tank to obtain a second residue and an extract B, d) processing the obtained second residue with the 80% ethanol in the steam jacketed rotary extractor for a time duration in the range of 100-140 minutes, followed by filtration in a separate clean, dry, and closed tank to obtain a third residue and an extract C, e) processing the obtained third residue with the 80% ethanol in the steam jacketed rotary extractor for a time duration in the range of 100-140 minutes, followed by filtration in a separate clean, dry, and closed tank to obtain a third residue and an extract D.

According to an another embodiment of the present invention, the proposed method comprises of following steps which includes: f) mixing obtained extract A, extract B, extract C, and extract D at a temperature in the range of 5-15° C. and holding for a time duration in the range of 20-28 hours in order to obtain a combined extract, followed by passing the obtained combined wash centrifuge having 3-5 micron nylon bag to remove insoluble fines and obtain a liquor, g) subjecting the obtained liquor to distillation under vacuum at a temperature in the range of 65-75° C. in a distillation kettle, followed by concentration of the liquor up to 25-30% TS (Total Solids) in order to obtain a concentrate, followed by holding the concentrate at a temperature of 10-15° C. for a time duration in the range of 20-28 hours for settling and filtering the concentrate through centrifuge to separate water insoluble solid mass and collect water soluble concentrate of phenolic compounds h) subjecting the obtained water soluble concentrate to spray drying using a spray drier having inner chamber fixed at a temperature in the range of 185-190° C. and outer chamber fixed at a temperature in the range of 90-105° C., in order to obtain sterilized pine bark extract, i) collecting the spray dried powder, grinding, and sieving with the powder through #150 sieve, passing the extract through metal detector to avoid Ferrous, Non-Ferrous and stainless steel elements, followed by HPLC analysis for proanthocyanidins content and packing the extract into fiber drums with double poly-bags for storage.

EXAMPLE

Referring to FIG. 1, a method for extraction of proanthocyanidins compound from pine bark extract—*Pinus roxburghii* is illustrated that comprises of following steps: a) a dried pine bark are weighed an pulverized, followed by sieving in order to obtain 10 # pulverized powder, b) 4 times of the 80% ethanol and RO (Reverse Osmosis) water are added in a jacketed rotary extractor at a temperature of 75° C. for a time duration of 120 minutes under circulation, followed by filtering through a filter in a clean, dry, and closed tank to obtain a first residue and an extract A, c) the first residue is added within the 80% of ethanol in the steam jacketed rotary extractor at a temperature of 75° C. for a time duration of 120 minutes, followed by filtration in a separate clean, dry, and closed tank to obtain a second residue and an extract B, d) the obtained second residue is processed with the 80% ethanol in the steam jacketed rotary extractor for a time duration of 120 minutes, followed by filtration in a separate clean, dry, and closed tank to obtain a third residue and an extract C, e) the obtained third residue is processed with the 80% ethanol in the steam jacketed rotary extractor for a time duration 120 minutes, followed by filtration in a separate clean, dry, and closed tank to obtain a third residue and an extract D.

The proposed method further comprises of following steps which includes: f) the obtained extract A, B, C, and D are mixed at a temperature of 10° C. and held for a time duration for 24 hours in order to obtain a combined extract, followed by passing the obtained combined wash centrifuge having 5 micron nylon bag to remove insoluble fines and obtain a liquor, g) the obtained liquor are subjected to distillation under vacuum at a temperature of 70° C. in a distillation kettle, followed by concentration of the liquor up to 25% TS (Total Solids) in order to obtain a concentrate, followed by holding the concentrate at a temperature of 10-15° C. for a time duration of 24 hours for settling and the concentrate is filtered through centrifuge to separate water insoluble solid mass and water soluble concentrate of phenolic compounds (proanthocyanidins) are collected, h) the obtained water soluble concentrate are subjected to spray drying using a spray drier having inner chamber fixed at a temperature in the range of 185-190° C. and outer chamber fixed at a temperature in the range of 90-105° C., in order to obtain sterilized pine bark extract, i) the spray dried powder are collected, grinded, and sieved with the powder through #150 sieve, passing the extract through metal detector to avoid Ferrous, Non-Ferrous and stainless steel elements, followed by HPLC analysis for proanthocyanidins content and packing the extract into fiber drums with double poly-bags for storage.

The dried pine bark used herein is obtained by collecting fresh bark of *Pinus roxburghii* tree from Pauri Garhwal region, removing outer scales of said bark, cleaning said bark from outer and inner side, and dried said cleaned bark under shade.

The insoluble solid mass obtain after filtration contains higher molecular weight oligomers of proanthocyanidins, whereas the water soluble concentrate contains phenolic acids, gallic acid, Protocatechuic acid, catechin, caffeic acid, taxifolin & ferulic acid, which is further subjected to spray drying.

The estimation of proanthocyanidins in said pine bark extract is carried out by High-performance liquid chromatography (HPLC) using an extract from *Pinus pinaster*, commercially available as maritime pine extract USP® as a reference standard. Proanthocyanidins content in Pine bark extract obtained from *Pinus roxburghii* is ≥80% by HPLC.

Characterization

The prepared extract was tested for the evaluation of physiochemical properties by executing the following tests-i) Analysis of modulatory property of the pine bark extract from *Pinus roxburghii* (Pinorox®) against hydrogen peroxide induced toxicity in human skin keratinocyte cells, comprising $H_2O_2$ induced cytotoxicity assay and GSH modulation assay ii) In-vitro evaluation of total antioxidant capacity of pine bark extract from *Pinus roxburghii* (Pinorox®) against the standard. Followed by randomized, parallel group, placebo-controlled trial study.

i) Analysis of Modulatory Property of the Pine Bark Extract from *Pinus roxburghii* (Pinorox®) Against Hydrogen Peroxide Induced Toxicity in Human Skin Keratinocyte Cells:

The modulatory activity of pine bark extract (powder) obtained from *Pinus roxburghii* (Pinorox®) was analyzed in order to evaluate the in—vitro activity on GSH (Glutathione) levels in Human skin keratinocyte cells and study the treatment of Human keratinocytes with hydrogen peroxide. Post the test analysis, it was found that hydrogen peroxide considerably increased the oxidative stress, thus reducing the GSH levels. However, the test sample which is pine bark extract powder demonstrated antioxidant property by significantly increasing the GSH levels in comparison to $H_2O_2$ control.

ii) Preparation of Test Solution (Pine Bark Extract):

For conducting the analysis, 10 mg of Pine bark extract from *Pinus roxburghii* (Pinorox®) was dissolved in a DMSO (Dimethyl sulfoxide) solution. The volume of the test solution was made up using DMEM-HG (Dulbecco's Modified eagle Medium) and supplemented with 2% inactivated FBS (Fetal bovine serum) to acquire a solution with concentration of 10 mg/ml. The test solution was further proceeded with sterilization using syringe filtration. For carrying out the cytotoxic analysis, a two-fold serial dilution was prepared.

iii) Preparation of Cell Line and Culture Medium

The cell line of Human keratinocytes (HaCaT) was obtained from Addex Bio, USA and were cultured in DMEM-HG supplemented media with 10% inactivated fetal bovine serum (FBS), penicillin (100 IU/mL), streptomycin (100 μl) and amphotericin B (5 μg/mL) in a wet atmosphere of 5% $CO_2$ at a temperature of 37° C. until confluent. The cells were later disintegrated with TPVG (Trypsin Phosphate Versene Glucose Solution) comprising (0.2% trypsin, 0.02% EDTA (Ethylenediaminetetraacetic acid), 0.05% glucose in PBS (Phosphate buffer solution). The stock culture was grown in a culture flask with a measurement of 25 cm2. All the experiments were conducted in a microtitre plate with 96 well.

iv) Induced Cytotoxicity Assay for $H_2O_2$:

A Cell monolayer was subjected to trypsinization and the cell count was adjusted to 2.0×105 cells/ml by using respective media (DMEM-HG) comprising FBS at 10%. The Pine bark extract from the *Pinus roxburghii* (Pinorox®) was assayed for the modulatory activity of GSH after the treatment with $H_2O_2$. In each plate of 12 well, diluted cell suspension of 1.0 ml was added. Post 24 hours, on the formation of monolayer, the supernatant was discarded and the monolayer was subjected to washing once with the medium. The cells were treated with $H_2O_2$ (500 μm) and was incubated for a duration of 3 hours followed by the addition of non-toxic concentrations of the test formulation (prepared in a medium with 2% FBS). Ascorbic acid was used as the positive control (standard) for the experiment at a concentration of 17.61 pg/mL.

The Pine Bark extract from *Pinus roxburghii* (Pinorox®) was assayed for in vitro Cytotoxicity study against HaCaT cell line by MTT assay. The cells were exposed to different concentrations of test substances (1000 μg/ml to 7.8 pg/ml). The Pinorox® formulation was found to be safe in HaCaT cells even at the highest concentration tested (1000 μg/mL). The Pine Bark extract from *Pinus roxburghii* (Pinorox®) at 500 μg/mL showed 182.23±0.02% and at 250 μg/mL exhibited 140.02±0.06% which is a remarkable increase in the levels of GSH compared to the standard tested i.e., Ascorbic acid which showed 95.59±0.03. The findings of the study suggest that Pine Bark extract from *Pinus roxburghii* (Pinorox®) could exhibit promising modulatory effect on GSH levels against hydrogen peroxide induced oxidative stress in a dose-dependent manner in Human keratinocytes.

v) Assay for GSH Modulation:

Referring to Table 1, a tabular representation of a *Pinus roxburghii*—Pine bark extract modulatory activity on GSH in a Hacat against hydrogen peroxide promoted oxidative stress is illustrated. The cell culture supernatant was collected from different treatment wells, centrifuged for 20 min at 1000 Xg at a temperature of 2-8° C. The samples were analyzed to estimate the levels of GSH using Elab science GSH ELISA kit by following the manufacturer's instruction. The graph shows the % increase in GSH level over $H_2O_2$ Control. Also, the modulatory effect by pine bark extract from *Pinus roxburghii* (Pinorox®) on GSH in a HaCat against hydrogen peroxide promoted oxidative stress is shown below in table no 1.

TABLE 1

*Pinus roxburghii* - Pine bark extract modulatory activity on GSH in a Hacat against hydrogen peroxide promoted oxidative stress

| SI. No | Samples | Tested Concentration | % Increase in GSH level over hydrogen peroxide control |
|---|---|---|---|
| 1. | *Pinus roxburghii* | 500 μg/ml | 182.23 ± 0.02 |
| | (Pinorox ®) | 250 μg/ml | 140.02 ± 0.06 |
| 2. | Ascorbic acid | 17.61 μg/ml | 95.59 ± 0.03 |

v) Estimation of Total Antioxidant Capacity (TAC) of a Test Substance:

The assay was performed to evaluate the total antioxidant capacity of a Pinorox® i.e. Pine bark extract from *Pinus roxburghii* against the standard ascorbic acid for in—vitro study. Antioxidants are compounds that are capable of inhibiting the process of oxidation that occurs under the influence of atmospheric oxygen or reactive oxygen species. The antioxidants are employed for stabilizing polymeric products, petrochemicals, cosmetics and food stuff along with pharmaceuticals. Antioxidants are involved in defense mechanisms of an organism against the associated pathologies in order to attack the free radicals. The test is carried out to check the total antioxidant capacity of a pine bark extract in order to avoid nutritional loss. The total antioxidant capacity of Pinorox® i.e. Pine bark extract from *Pinus roxburghii* was found out to be 756.993±0.150 mM equivalent of the ascorbic acid having 1000±0.027 mM at 1000 μg/mL.

vi) Test Substance and Standard Preparation:

Pine bark extract of 5.5 mg each/ascorbic acid were subjected to dissolve in 0.5 ml of DMSO (Dimethyl sulfoxide) in a separate container. 0.244 ml of 0.6 M sulphuric acid was added to a 15 ml of distilled water. 0.334 g of 28 mM sodium phosphate along with 0.074 g of 4 mM ammonium molybdate was added to the solution and was completely dissolved.

vii) Assay for Estimating Total Antioxidant Capacity of Pine Bark Extract

Referring to Table 2, a tabular representation of a total antioxidant capacity in a Pine Bark Extract is illustrated. Test solution of 0.1 ml and a standard containing a reducing species in DMSO were taken in a separate Eppendorf tube, and reagent solution of 1 ml comprising (0.6M sulphuric acid, 28 mM sodium phosphate and 4 mM ammonium molybdate) was added and subjected to incubation in a water bath for 90 minutes at 95° C. Post this, the samples were maintained to room temperature and 0.1 ml was pipette out in triplicates to a microtitre plate. The reagent solution is used as a blank. The absorbance was recorded at 490 mm via ELISA (enzyme-linked immunosorbent assay) reader and the values were recorded. The total activity of antioxidant was expressed as mM which is equivalent of ascorbic acid. The table no 2 representation of the total antioxidant capacity in a test substance.

TABLE 2

The total antioxidant capacity in a Pine Bark Extract was demonstrated as mentioned below in a tabular format

| SI. NO | Test substance | Concentration (µg/ml) | TAC |
|---|---|---|---|
| 1 | Pine bark extract from *Pinus roxburghii* (Pinorox ®) | 1000 | 756.993 ± 0.150 |
| 2 | Ascorbic acid | 1000 | 1000 ± 0.027 |

viii) Estimation of Proanthocyanidins by HPLC:

Chromatograpahic Condition:

- Column: Luna C18, 100 Å (250 mm×4.6 mm, 5µ) or equivalent
- Detector: UV, 280 nm
- Flow rate: 1.0 ml/minute
- Injection Volume: 10 µL
- Column temperature: 400 C
- LC Mode: Low pressure gradient
- Mobile Phase Preparation A: 100% Methanol.
- Mobile phase preparation B: dilute 1.0 g of orthophosphoric acid in 1000 ml of water, mix well and filter through 0.45 µm fine pore size, degas and sonicate at least 5 minutes.

Referring to Table 3, a tabular representation of a gradient program of HPLC is illustrated.

TABLE 3

Gradient program of HPLC

| Time (min) | Mobile Phase A (%) | Mobile Phase B (% ) |
|---|---|---|
| 0.01 | 8 | 92 |
| 40.00 | 34 | 66 |
| 45.00 | 2 | 98 |
| 50.00 | 2 | 98 |
| 51.00 | 92 | 8 |
| 57.00 | 92 | 8 |
| 58.00 | 8 | 92 |
| 65.00 | 8 | 92 |
| 65.01 | Control | Stop |

Standard Solution Preparation:

Weigh accurately about 50 mg of maritime pine extract reference standard or 35.5 mg equivalent to reference standard) in 25 ml volumetric flak. Add 20 ml of Methanol and sonicate to dissolve completely. Make up the volume up to 25 ml with Methanol. Filter through 0.45 µm nylon syringe filter. Discard the first few ml of filtrate.

Sample Solution Preparation for Extract:

Weigh accurately about 100 mg of extract (or 71.0 mg equivalent to reference standard) in 50 mL volumetric flask. Add 30 mL of methanol and sonicate to dissolve completely. Make up the volume up to 50 mL with methanol. Filter through a 0.45 µm nylon syringe filter. Discard the first few mL of filtrate.

Sample Preparation for Bark:

Weigh accurately about 2.0 g grinder powder of pine bark in 250 mL round bottom flask, add 50 ml of methanol and reflux in water bath for 1 Hrs., and allow to cool at room temperature, decant, and retain the solvent. Repeat until the solvent is colorless. Combine the retained solvents, filter, concentrate under vacuum to about 90 ml, transfer to a 100 ml volumetric flask, and adjust the volume with methanol. Dilute 5 ml of this solution into 50 ml volumetric flask and make up volume with methanol, before injection filter the solution through 0.45 µm nylon syringe filter.

System Suitability Criteria:

The % RSD of Sum of the total peak area of Gallic acid, Protocatechuic Acid, Catechin, Caffeic Acid, Taxifolin and Ferulic Acid from the Standard solution five injections should not be more than 5.0% Calculate the percentage of Oligomeric Proanthocyanidins in the portion of Pine bark extract.

Calculation:

$$\text{Result } (\%) = \frac{rV}{rS} \times \frac{Cs}{Ct} \times P$$

Where, rV=Sum of the total peak areas of Gallic Acid, Protocatechuic Acid,

Catechin, caffeic Acid, Taxifolin and Ferulic Acid from the sample solution.

rS=Sum of the total peak areas of Gallic Acid, Protocatechuic Acid, Catechin, caffeic Acid, Taxifolin and Ferulic Acid from the standard solution.

Cs=Concentration of standard solution.

Ct=Concentration of sample solution.

P=Purity of maritime pine extract.

Figure 2:
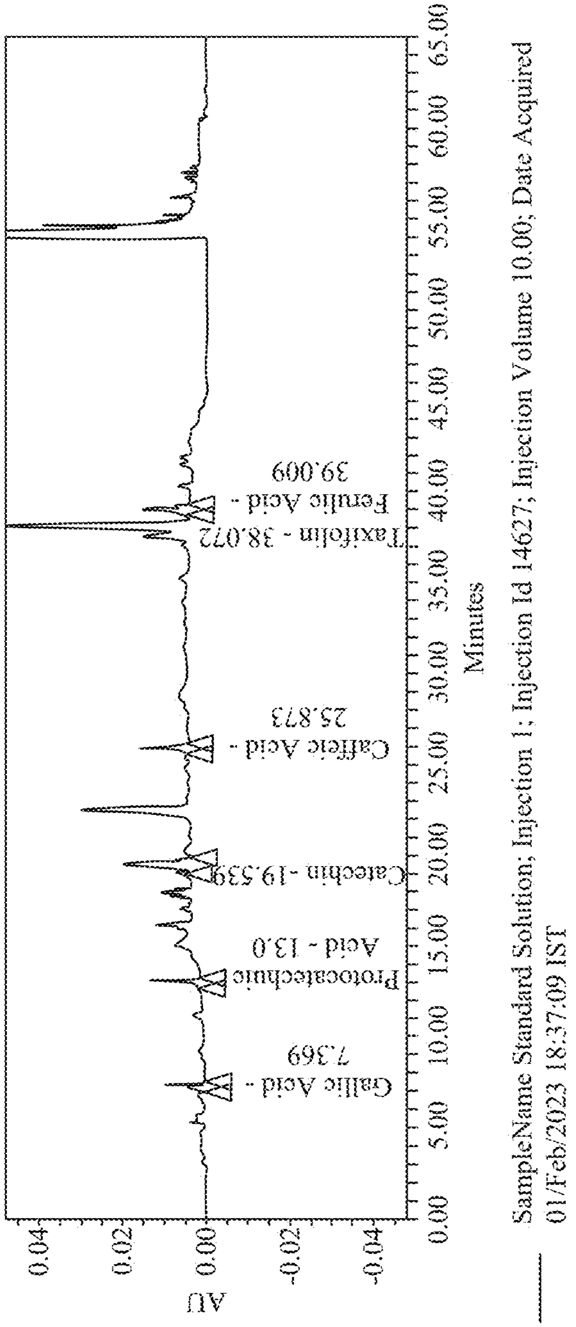
FIG. 2 illustrates a graphical representation of a HPLC of standard solution: Injection 1.

Referring to FIG. 2, a graphical representation of a HPLC of standard solution: Injection 1 is illustrated.

Figure 3:
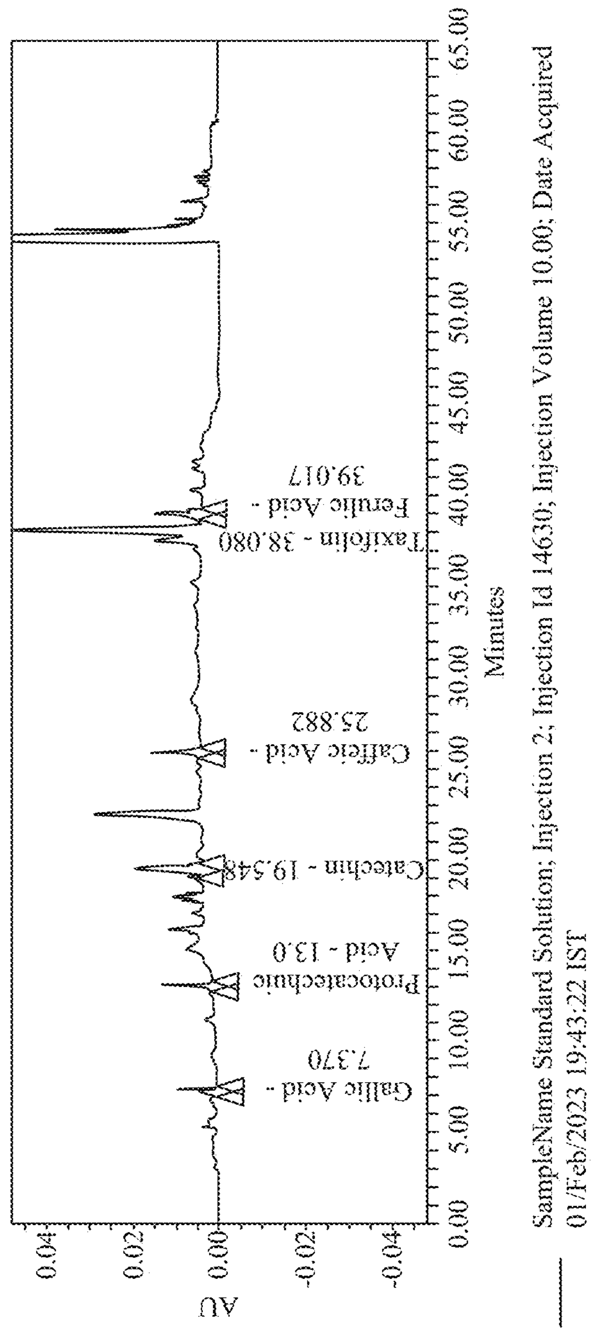
FIG. 3 illustrates a graphical representation of a HPLC of standard solution: Injection.

Referring to FIG. 3, a graphical representation of a HPLC of standard solution: Injection 2 is illustrated.

Figure 4:
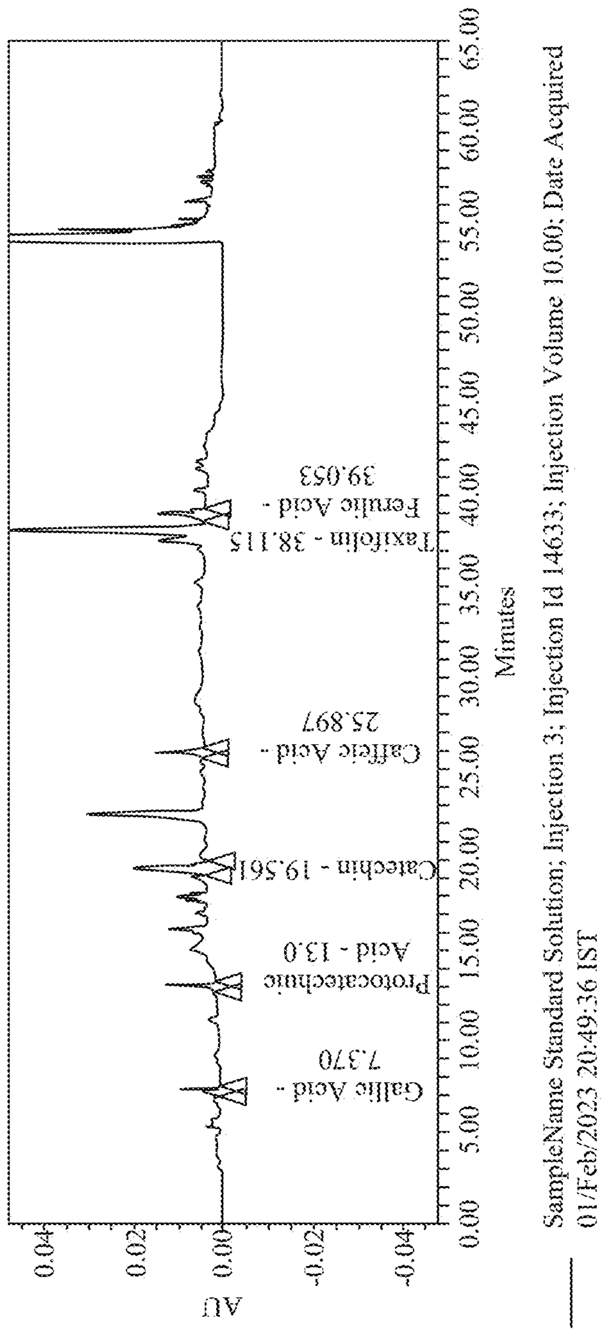
FIG. 4 illustrates a graphical representation of a HPLC of standard solution: Injection 3.

Referring to FIG. 4, a graphical representation of a HPLC of standard solution: Injection 3 is illustrated.

Figure 5:
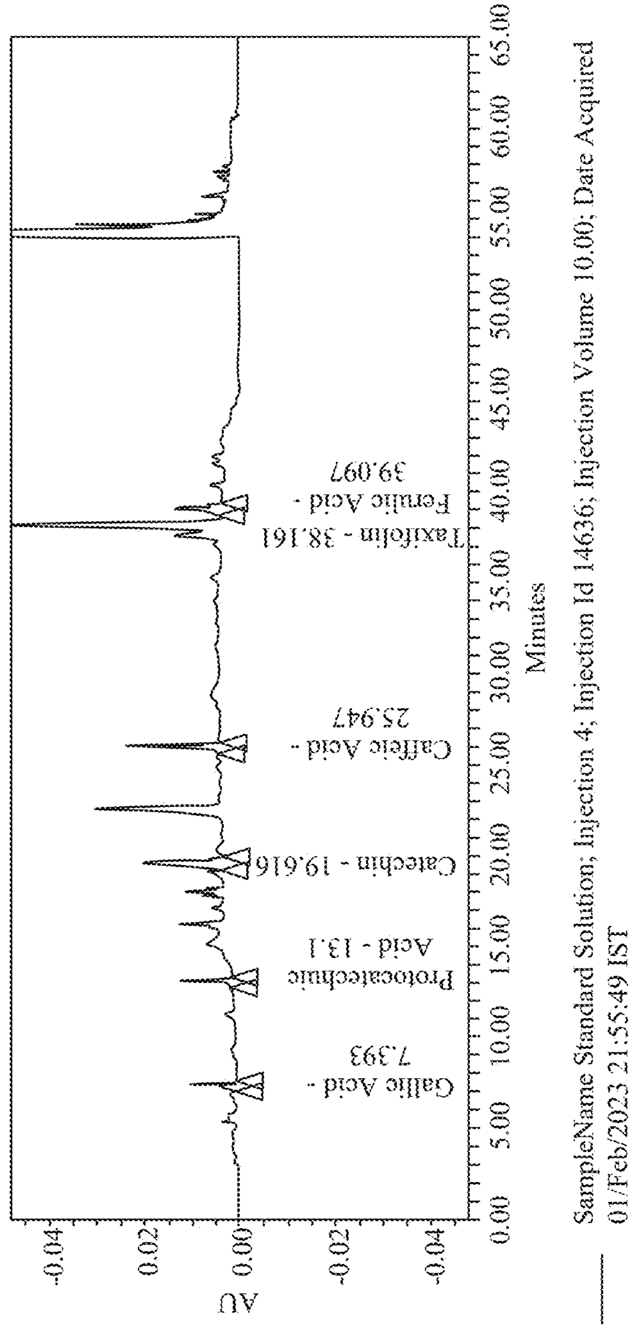
FIG. 5 illustrates a graphical representation of a HPLC of standard solution: Injection 4.

Referring to FIG. 5, a graphical representation of a HPLC of standard solution: Injection 4 is illustrated.

Figure 6:
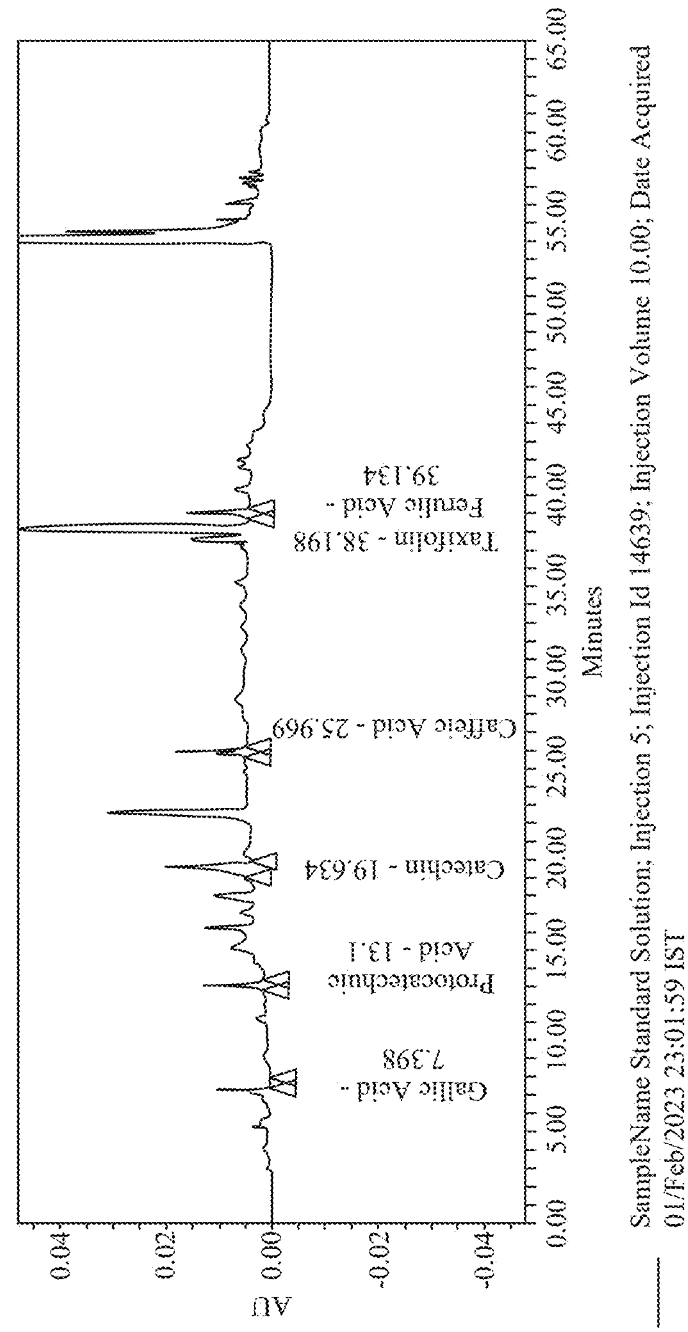
FIG. 6 illustrates a graphical representation of a HPLC of standard solution: Injection 5.

Referring to FIG. 6, a graphical representation of a HPLC of standard solution: Injection 5 is illustrated.

Referring to Table 4, a tabular representation of a component summary table name of caffeic acid is illustrated.

TABLE 4

Component summary table name of caffeic acid

| | Sample Name | Vial | Inj | Name | RT | Area | % Area | USP ® Plate Count | USP ® Tailing | Int Type | Total Area |
|---|---|---|---|---|---|---|---|---|---|---|---|
| 1 | Standard Solution | 2 | 1 | Caffeic Acid | 25.873 | 122975 | 9.40 | 50633 | 1.0 | BB | 1308730 |

TABLE 4-continued

| Component summary table name of caffeic acid | | | | | | | | | | | |
|---|---|---|---|---|---|---|---|---|---|---|---|
| | Sample Name | Vial | Inj | Name | RT | Area | % Area | USP ® Plate Count | USP ® Tailing | Int Type | Total Area |
| 2 | Standard Solution | 2 | 2 | Caffeic Acid | 25.882 | 123455 | 9.44 | 50993 | 1.0 | BB | 1308065 |
| 3 | Standard Solution | 2 | 3 | Caffeic Acid | 25.897 | 123433 | 9.38 | 50964 | 1.0 | BB | 1316318 |
| 4 | Standard Solution | 2 | 4 | Caffeic Acid | 25.947 | 123850 | 9.38 | 51555 | 1.0 | BB | 1319738 |
| 5 | Standard Solution | 2 | 5 | Caffeic Acid | 25.969 | 124094 | 9.38 | 51194 | 1.0 | BB | 1322652 |
| Mean | | | | | 25.913 | 123561 | | | | | 1315100 |
| % RSD | | | | | 0.2 | 0.3 | | | | | 0.5 |

Referring to Table 5, a tabular representation of a component summary table name of Catechin is illustrated.

TABLE 5

| Component summary table name of Catechin | | | | | | | | | | | |
|---|---|---|---|---|---|---|---|---|---|---|---|
| | Sample Name | Vial | Inj | Name | RT | Area | % Area | USP ® Plate Count | USP ® Tailing | Int Type | Total Area |
| 1 | Standard Solution | 2 | 1 | Catechin | 19.539 | 228711 | 17.48 | 18801 | 0.8 | BB | 1308730 |
| 2 | Standard Solution | 2 | 2 | Catechin | 19.548 | 227832 | 17.42 | 19238 | 0.8 | BB | 1308065 |
| 3 | Standard Solution | 2 | 3 | Catechin | 19.561 | 230252 | 17.49 | 18378 | 0.8 | BB | 1316318 |
| 4 | Standard Solution | 2 | 4 | Catechin | 19.616 | 230286 | 17.45 | 18584 | 0.8 | BB | 1319738 |
| 5 | Standard Solution | 2 | 5 | Catechin | 19.634 | 231311 | 17.49 | 18558 | 0.8 | BB | 1322652 |
| Mean | | | | | 19.580 | 229678 | | | | | 1315100 |
| % RSD | | | | | 0.2 | 0.6 | | | | | 0.5 |

Referring to Table 6, a tabular representation of a component summary table name of Ferulic Acid is illustrated.

TABLE 6

| Component summary table name of Ferulic Acid | | | | | | | | | | | |
|---|---|---|---|---|---|---|---|---|---|---|---|
| | Sample Name | Vial | Inj | Name | RT | Area | % Area | USP ® Plate Count | USP ® Tailing | Int Type | Total Area |
| 1 | Standard Solution | 2 | 1 | Ferulic Acid | 39.009 | 116081 | 8.87 | 111740 | 1.0 | BB | 1308730 |
| 2 | Standard Solution | 2 | 2 | Ferulic Acid | 39.017 | 115417 | 8.82 | 112359 | 1.0 | BB | 1308065 |
| 3 | Standard Solution | 2 | 3 | Ferulic Acid | 39.053 | 117245 | 8.91 | 111785 | 1.0 | BB | 1316318 |
| 4 | Standard Solution | 2 | 4 | Ferulic Acid | 39.097 | 117820 | 8.93 | 112229 | 1.0 | BB | 1319738 |
| 5 | Standard Solution | 2 | 5 | Ferulic Acid | 39.134 | 118275 | 8.94 | 113177 | 1.0 | BB | 1322652 |
| Mean | | | | | 39.062 | 116968 | | | | | 1315100 |
| % RSD | | | | | 0.1 | 1.0 | | | | | 0.5 |

Referring to Table 7, a tabular representation of a component summary table name of Gallic Acid is illustrated.

TABLE 7

Component summary table name of Gallic Acid

| | Sample Name | Vial | Inj | Name | RT | Area | % Area | USP ® Plate Count | USP ® Tailing | Int Type | Total Area |
|---|---|---|---|---|---|---|---|---|---|---|---|
| 1 | Standard Solution | 2 | 1 | Gallic Acid | 7.369 | 87230 | 6.67 | 4680 | 0.7 | BB | 1308730 |
| 2 | Standard Solution | 2 | 2 | Gallic Acid | 7.370 | 87495 | 6.69 | 4547 | 0.7 | BB | 1308065 |
| 3 | Standard Solution | 2 | 3 | Gallic Acid | 7.370 | 88029 | 6.69 | 4771 | 0.7 | BB | 1316318 |
| 4 | Standard Solution | 2 | 4 | Gallic Acid | 7.393 | 87255 | 6.61 | 4734 | 0.7 | BB | 1319738 |
| 5 | Standard Solution | 2 | 5 | Gallic Acid | 7.398 | 87619 | 6.62 | 4529 | 0.7 | BB | 1322652 |
| Mean | | | | | 7.380 | 87526 | | | | | 1315100 |
| % RSD | | | | | 0.2 | 0.4 | | | | | 0.5 |

Referring to Table 8, a tabular representation of a component summary table name of Protocatechuic Acid is illustrated.

TABLE 8

Component summary table name of Protocatechuic Acid

| | Sample Name | Vial | Inj | Name | RT | Area | % Area | USP ® Plate Count | USP ® Tailing | Int Type | Total Area |
|---|---|---|---|---|---|---|---|---|---|---|---|
| 1 | Standard Solution | 2 | 1 | Protocatechuic Acid | 13.072 | 71463 | 5.46 | 16687 | 0.9 | BB | 1308730 |
| 2 | Standard Solution | 2 | 2 | Protocatechuic Acid | 13.080 | 71631 | 5.48 | 17154 | 0.9 | BB | 1308065 |
| 3 | Standard Solution | 2 | 3 | Protocatechuic Acid | 13.083 | 71457 | 5.43 | 16832 | 0.9 | BB | 1316318 |
| 4 | Standard Solution | 2 | 4 | Protocatechuic Acid | 13.118 | 72019 | 5.46 | 16682 | 0.9 | BB | 1319738 |
| 5 | Standard Solution | 2 | 5 | Protocatechuic Acid | 13.130 | 73002 | 5.52 | 16726 | 0.9 | BB | 1322652 |
| Mean | | | | | 13.096 | 71915 | | | | | 1315100 |
| % RSD | | | | | 0.2 | 0.9 | | | | | 0.5 |

Referring to Table 9, a tabular representation of a component summary table name of Taxifolin is illustrated.

TABLE 9

Component summary table name of Taxifolin

| | Sample Name | Vial | Inj | Name | RT | Area | % Area | USP ® Plate Count | USP ® Tailing | In Type | Total Area |
|---|---|---|---|---|---|---|---|---|---|---|---|
| 1 | Standard Solution | 2 | 1 | Taxifolin | 38.072 | 682268 | 52.13 | 111483 | 1.0 | BB | 1308730 |
| 2 | Standard Solution | 2 | 2 | Taxifolin | 38.080 | 682234 | 52.16 | 111910 | 1.0 | BB | 1308065 |
| 3 | Standard Solution | 2 | 3 | Taxifolin | 38.115 | 685902 | 52.11 | 112266 | 1.0 | BB | 1316318 |
| 4 | Standard Solution | 2 | 4 | Taxifolin | 38.161 | 688508 | 52.17 | 112124 | 1.0 | BB | 1319738 |
| 5 | Standard Solution | 2 | 5 | Taxifolin | 38.198 | 688351 | 52.04 | 112814 | 1.0 | BB | 1322652 |
| Mean | | | | | 38.125 | 685453 | | | | | 1315100 |
| % RSD | | | | | 0.1 | 0.5 | | | | | 0.5 |

Figure 7:
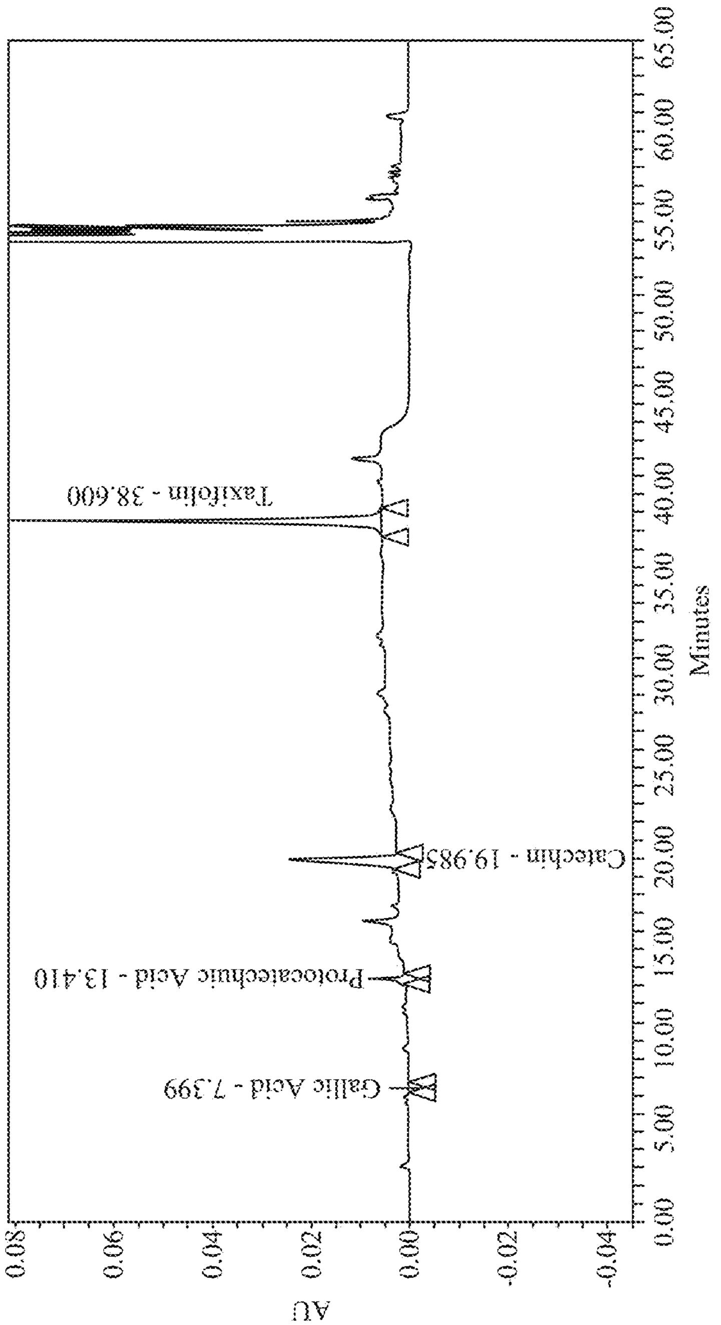
FIG. 7 illustrates a graphical representation of a HPLC of a pine bark extract sample level 1.

Referring to FIG. 7, a graphical representation of a HPLC of a pine bark extract sample level 1 is illustrated.

Referring to Table 10, a tabular representation of a HPLC of level 1 of a pine bark extract is illustrated.

TABLE 10

| HPLC of level 1 of a pine bark extract | | | | | | |
|---|---|---|---|---|---|---|
| Peak Name | RT | Height (μV) | Area | Int Type | USP ® Plate Count | USP ® Tailing |
| 1 Total Area | | 94549 | 1780835 | Group | | |
| 2 Gallic Acid | 7.399 | 102 | 1447 | BB | 6244 | 1.3 |
| 3 Proto-catechuic Acid | 13.410 | 3364 | 50494 | BB | 17311 | 0.9 |
| 4 Catechin | 19.985 | 17764 | 365544 | BB | 18085 | 0.8 |
| 5 Caffeic Acid | 26.127 | | | Missing | | |
| 6 Taxifolin | 38.600 | 73318 | 1363349 | BB | 99634 | 0.9 |
| 7 Ferulic Acid | 39.500 | | | Missing | | |

Figure 8:
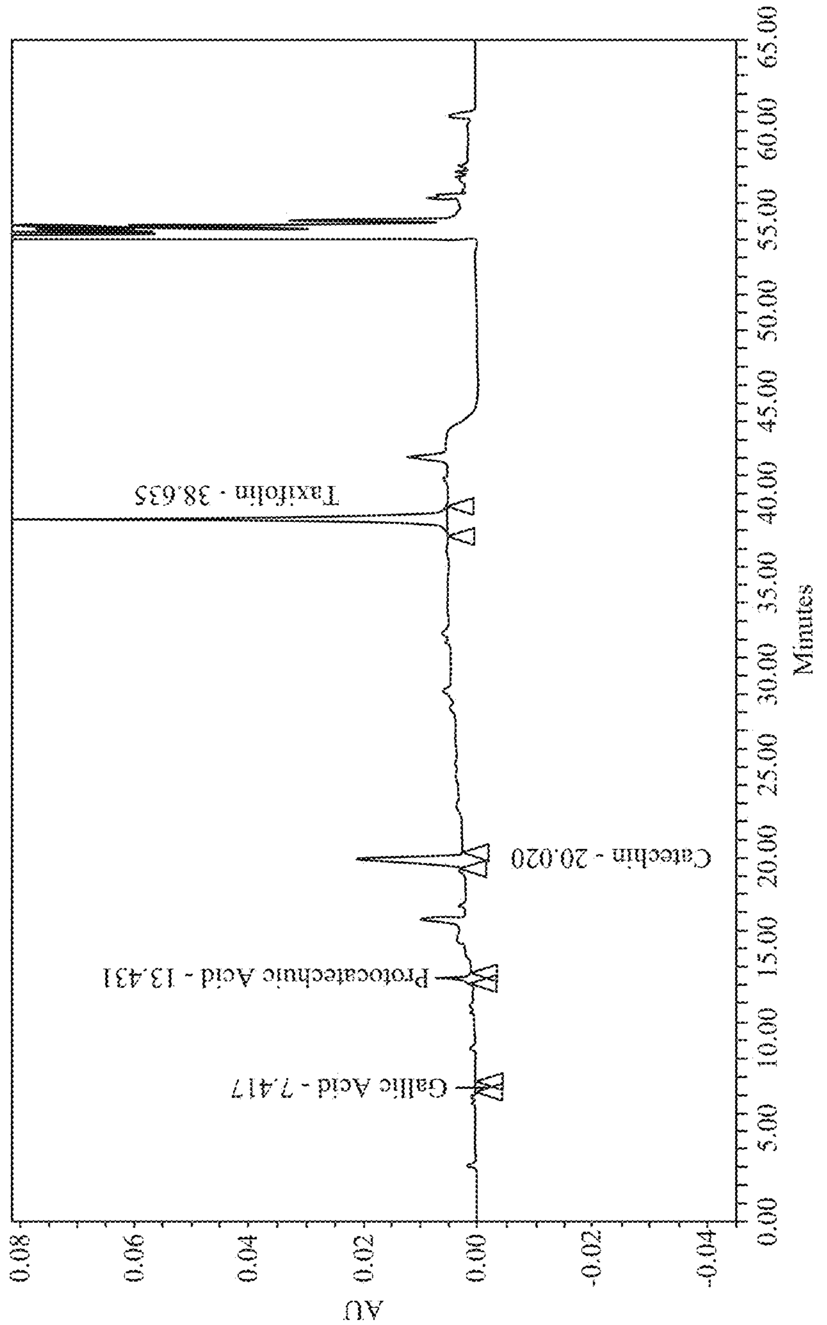
FIG. 8 illustrates a graphical representation of a HPLC of a pine bark extract sample level 2.

Referring to FIG. 8, a graphical representation of a HPLC of a pine bark extract sample level 2 is illustrated.

Referring to Table 11, a tabular representation of a HPLC of level 2 of a pine bark extract is illustrated.

TABLE 11

| HPLC of level 2 of a pine bark extract | | | | | | |
|---|---|---|---|---|---|---|
| Peak Name | RT | Height (μV) | Area | Int Type | USP ® Plate Count | USP ® Tailing |
| 1 Total Area | | 93809 | 1770563 | Group | | |
| 2 Gallic Acid | 7.417 | 103 | 1408 | BB | 7231 | 1.3 |
| 3 Proto-catechuic Acid | 13.431 | 3351 | 50963 | BB | 17092 | 0.9 |
| 4 Catechin | 20.020 | 17673 | 362789 | BB | 18237 | 0.8 |
| 5 Caffeic Acid | 26.127 | | | Missing | | |
| 6 Taxifolin | 38.635 | 72682 | 1355403 | BB | 99144 | 0.9 |
| 7 Ferulic Acid | 39.500 | | | Missing | | |

Figure 9:
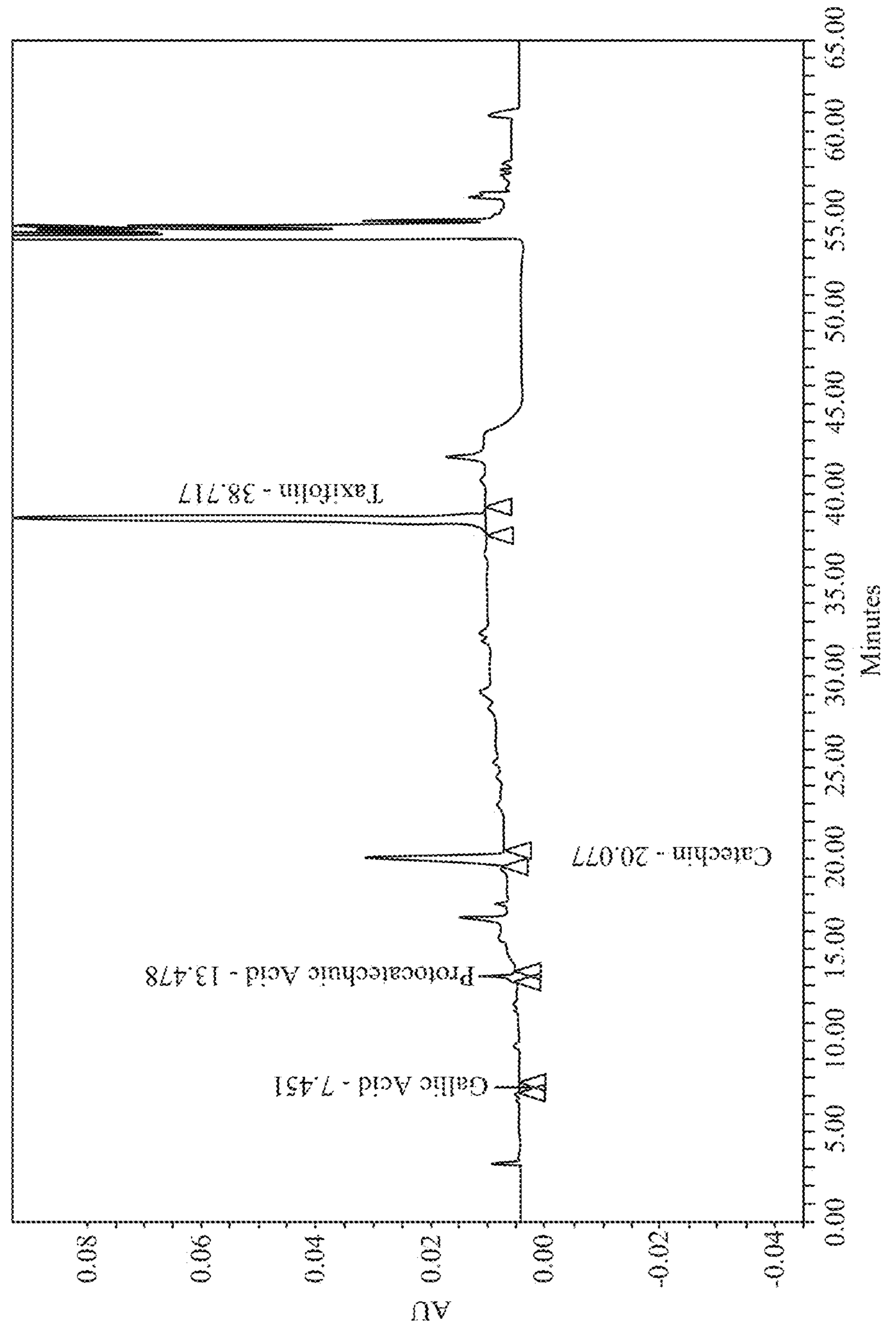
FIG. 9 illustrates a graphical representation of a HPLC of a pine bark extract sample level 3.

Referring to FIG. 9, a graphical representation of a HPLC of a pine bark extract sample level 3 is illustrated.

Referring to Table 12, a graphical representation of a HPLC of a pine bark extract sample level 3 is illustrated.

TABLE 12

| HPLC of a pine bark extract sample level 3 | | | | | | |
|---|---|---|---|---|---|---|
| Peak Name | RT | Height (μV) | Area | Int Type | USP ® Plate Count | USP ® Tailing |
| 1 Total Area | | 95346 | 1790637 | Group | | |
| 2 Gallic Acid | 7.451 | 99 | 1414 | BB | 6401 | 1.3 |
| 3 Proto-catechuic Acid | 13.478 | 3383 | 51081 | BB | 17443 | 0.9 |
| 4 Catechin | 20.077 | 17993 | 367648 | BB | 18797 | 0.8 |
| 5 Caffeic Acid | 26.127 | | | Missing | | |
| 6 Taxifolin | 38.717 | 73870 | 1370494 | BB | 100587 | 0.9 |
| 7 Ferulic Acid | 39.500 | | | Missing | | |

viii) Evaluation of Clinical Trial to Study the Safety and Efficacy of Pine Bark Extract:

A potential, double blind, placebo comparative, interventional clinical study was conducted to evaluate the efficacy and safety of Pinorox® for improving physical and athletic performance in normal and sports subjects. The study parameters are mentioned below.

Volunteer Health Condition and the Problem Studied (Placebo Study)

Healthy sedentary volunteers of age group 18 years to 40 years following (Daily routine with no or little exercises) and sports subjects (Average in more than 3 sessions per week). A comparator agent namely placebo each capsule containing 200 mg of Maltodextrin Route: (Oral) was given daily once after a meal or in between the meals for a period of 90 days. The precaution to be followed while studying the volunteers was to avoid the intake of medicine on empty stomach. The intervention acquired from the study was that each capsule contains 200 mg pine bark extract that is Pinorox® given to the volunteers once in a day daily after meal or between the meals for 90 days. The precaution to be followed while studying the volunteers was to avoid the intake of medicine on empty stomach.

Brief Overview of the Placebo Study (Details Pertaining to the Volunteers)

Volunteers from age group comprising of 18-40 years with BMI between 18.0-24.9 kg/m$^2$ were selected for conducting the study. The sedentary subjects were mentally, physically and legally eligible to give their informed consent for participating in a study trial. The healthy sedentary consists of both male and female subjects following (Daily routine with no or little exercises) and sports subjects following the routine as same as healthy sedentary subjects with (Average in more than 3 sessions per week) change. The patient voluntarily agreed to comply with all trial requirement. The selected patents who were chosen for the trial had not participated in a similar investigation in the past last three months. During the trial the subject was in good health and appropriate fit for exercise. The subject agreed to not use any dietary or herbal supplements and maintain their normal dietary intake until the study completion and also agreed to avoid consumption of anti-oxidant rich food. In addition to this, the subjects were instructed to refrain from exercise, 48 hours prior to the experiment and had to fast two hours before. The subject should have normal haematology and biochemistry ranges.

Computer Generated Randomization Study Trial

In this clinical study trial, the participant and investigator were blinded. The total sample size for studying the trial was 50. The primary outcome of the trial states that a change was reported in baseline in the rate of oxygen consumption $VO_2$ max (endurance) in comparison to the placebo study. The baseline time point for the study was 30, 60 and 90 days. The outcome was assessed on the basis of anaerobic power and rate of fatigue by the use of Wingate test. The Wingate test measures the anaerobic power peak achieved during the commencement of the test. Basically, the test talks about the anaerobic capacity produced over the entire 30-second period including the fatigue index in the test. The secondary outcome drawn from the trial enlists the change in assessment values by the use of 1-RM test and the baseline along with the day was 90. Secondary outcome also comprises of a questionnaire assessment on quality of life using SF-36. SF-36 is a questionnaire that measures eight main parameters comprising vitality (VT), bodily pain (BP), general health (GH), physical functioning (PF), role physical (RP), social functioning (SF), role emotional (RE), and mental health (MH). The last outcome or the tertiary outcome of the trial talks about the laboratory tests including CBC (Complete Blood count) and the level of serum creatinine, SGOT serum glutamic-oxaloacetic transaminase test is a type of blood test that targets on profiling the functionality of liver and SGPT test that stands for serum glutamic Pyruvic Transaminase. The test is executed to measure the glutamate pyruvate transaminase (GPT) amount in the blood serum.

Therefore, the pine bark extract obtained from *Pinus roxburghii* having an antioxidant property, which can be used in the nutraceutical or health/dietary supplement having functional application as an antioxidant.

Although the field of the invention has been described herein with limited reference to specific embodiments, this description is not meant to be construed in a limiting sense. Various modifications of the disclosed embodiments, as well as alternate embodiments of the invention, will become apparent to persons skilled in the art upon reference to the description of the invention.

We claim:

1. A method for extraction of a pine bark extract comprising phenolic compounds from pine bark of *Pinus roxburghii*, comprising the steps:

i) weighing and pulverizing dried pine bark, followed by sieving to obtain pulverized powder;

ii) adding 80% ethanol and 20% RO (Reverse Osmosis) water in said pulverized powder in a steam jacketed rotary extractor and carrying out extraction under circulation at a temperature in the range of 70-80° C. for a time duration in the range of 100-140 minutes, followed by filtering through a filter to obtain a first residue and an extract A;

iii) adding said first residue with said 80% ethanol in said steam jacketed rotary extractor at a temperature in the range of 70-80° C. for a time duration in the range of 100-140 minutes, followed by filtration in a closed tank to obtain a second residue and an extract B;

iv) processing said obtained second residue with said 80% ethanol in said steam jacketed rotary extractor for a time duration in the range of 100-140 minutes, followed by filtration in a closed tank to obtain a third residue and an extract C;

v) processing said obtained third residue with said 80% ethanol in said steam jacketed rotary extractor for a time duration in the range of 100-140 minutes, followed by filtration in a separate clean, dry, and closed tank to obtain a fourth residue and an extract D;

vi) mixing said obtained extract A, extract B, extract C, and extract D at a temperature in the range of 5-15° C. and holding for a time duration in the range of 20-28 hours in order to obtain a combined extract, followed by filtering said obtained combined extract through a centrifuge fitted with 3-5 micron nylon bag to remove insoluble fines and obtain a liquor;

vii) subjecting said obtained liquor to distillation under vacuum at a temperature in the range of 65-75° C. in a distillation kettle, making final concentration of said liquor up to 25-30% TS (Total Solids) in order to obtain a concentrate, followed by holding said concentrate at a temperature of 10-15° C. for a time duration in the range of 20-28 hours for settling and filtering said concentrate through a centrifuge to separate water insoluble solid mass and collect water soluble concentrate of phenolic compounds viii) subjecting said obtained water soluble concentrate to spray drying using a spray drier having inner chamber fixed at a temperature in the range of 185-190° C. and outer chamber fixed at a temperature in the range of 90-105° C., in order to obtain sterilized pine bark extract in spray dried powder form; and ix) collecting said spray dried powder, grinding, and sieving said powder through #150 sieve, passing said extract through metal detector to avoid ferrous, non-ferrous, and stainless-steel elements, followed by HPLC analysis for phenolic compound content and packing said extract into fiber drums with double polybags for storage of said extract, wherein steps ii) and iii) are each carried out at a temperature of about 75° C. for a time duration of about 120 minutes, and steps iv) and v) are each carried out for a time duration of about 120 minutes.

2. The method as claimed in claim 1, wherein said dried pine bark is obtained by collecting fresh bark of *Pinus roxburghii* tree, removing outer scales of said bark, cleaning said bark from outer and inner side, and drying said cleaned bark under shade.

3. The method as claimed in claim 1, wherein estimation of proanthocyanidins-phenolic compound content including phenolic acids, gallic acid, protocatechuic acid, catechin, caffeic acid, taxifolin, and ferulic acid in said pine bark extract is carried out by High-performance liquid chromatography (HPLC) using a maritime pine (*Pinus pinaster*) extract as a reference standard.

* * * * *